(12) United States Patent
Katsuki et al.

(10) Patent No.: US 8,372,429 B2
(45) Date of Patent: *Feb. 12, 2013

(54) AGENT FOR TREATING ULCER

(75) Inventors: Keiko Katsuki, Sakaide (JP); Akira Okada, Sakaide (JP)

(73) Assignee: Kyowa Chemical Industry Co., Ltd., Takamatsu-shi (JP)

(*) Notice: Subject to any disclaimer, the term of this patent is extended or adjusted under 35 U.S.C. 154(b) by 180 days.

This patent is subject to a terminal disclaimer.

(21) Appl. No.: 12/746,143

(22) PCT Filed: Dec. 4, 2008

(86) PCT No.: PCT/JP2008/072016
§ 371 (c)(1), (2), (4) Date: Aug. 20, 2010

(87) PCT Pub. No.: WO2009/075216
PCT Pub. Date: Jun. 18, 2009

(65) Prior Publication Data
US 2010/0323032 A1     Dec. 23, 2010

(30) Foreign Application Priority Data

Dec. 10, 2007  (JP) .................................. 2007-318529
Apr. 30, 2008  (JP) .................................. 2008-118043

(51) Int. Cl.
A61K 9/20      (2006.01)
A61K 33/30     (2006.01)

(52) U.S. Cl. ............... 424/464; 423/593.1; 423/594.14; 514/819; 514/925; 514/926

(58) Field of Classification Search ......................... None
See application file for complete search history.

(56) References Cited

U.S. PATENT DOCUMENTS

| 3,539,306 A | 11/1970 | Kumura et al. |
| 3,650,704 A | 3/1972 | Kumura et al. |
| 5,741,526 A | 4/1998 | Miyata |
| 5,750,609 A | 5/1998 | Nosu et al. |
| 6,287,532 B1 | 9/2001 | Okada et al. |
| 6,297,193 B1 | 10/2001 | Miyata |
| 6,313,208 B1 | 11/2001 | Nosu et al. |

| 2002/0006375 A1 | 1/2002 | Okada et al. | |
| 2004/0229987 A1* | 11/2004 | Kobayashi et al. | ........... 524/424 |
| 2009/0142394 A1* | 6/2009 | Okada et al. | ................. 424/465 |

FOREIGN PATENT DOCUMENTS

| JP | 46-2280 B | 1/1971 |
| JP | 50-30039 B | 9/1975 |
| JP | 6-49035 A | 2/1994 |
| JP | 8-291011 A | 11/1996 |
| JP | 8-337768 A | 12/1996 |
| JP | 10-182315 A | 7/1998 |
| JP | 11-180808 | 7/1999 |
| JP | 11-222494 A | 8/1999 |
| JP | 11-240886 A | 9/1999 |
| JP | 2000-159520 A | 6/2000 |
| JP | 2004-225052 A | 8/2004 |
| JP | 2006-131581 A | 5/2006 |
| JP | 2008-120703 A | 5/2008 |
| WO | WO 2008/075621 A1 | 6/2008 |

OTHER PUBLICATIONS

Frommer, "The Healing of Gastric Ulcers by Zinc Sulphate", The Medical Journal of Australia, Nov. 22, 1975, vol. 2, No. 21, pp. 793-796.

Kawamura et al., "Suppressive Effect of Antiulcer Agents on Granulocytes—A Role for Granulocytes in Gastric Ulcer Formation", Digestive Diseases and Sciences, vol. 45, No. 9, Sep. 2000, pp. 1786-1791.

Hung, "Importance of Histamine, Glutathione and Oxyradicals in Modulating Gastric Haemorrhagic Ulcer in Septic Rats", Clinical and Experimental Pharmacology and Physiology, vol. 27, pp. 306-312, 2000, XP002613924.

Supplementary European Search Report for Application No. 08859116 dated Dec. 22, 2010.

* cited by examiner

*Primary Examiner* — Lakshmi Channavajjala
(74) *Attorney, Agent, or Firm* — Birch, Stewart, Kolasch & Birch, LLP

(57) ABSTRACT

An agent for treating ulcer containing, as an effective component, a particulate composite hydrotalcite obtained by solidly dissolving a small amount of zinc in the particulate hydrotalcite, exhibiting excellent effect for treating the peptic ulcer and, further, working as a Zn-supplying agent. The agent for treating the ulcer is represented by the following formula (1),

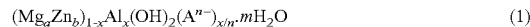

$$(Mg_a Zn_b)_{1-x} Al_x (OH)_2 (A^{n-})_{x/n} \cdot m H_2 O \quad (1)$$

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.1 \leq a < 1$, $0 < b \leq 0.5$, $0 \leq m < 1$.

7 Claims, No Drawings

AGENT FOR TREATING ULCER

TECHNICAL FIELD

This invention relates to an agent for treating ulcer containing a particulate composite hydrotalcite as an effective component. More particularly, the invention relates to a novel agent for treating ulcer using a zinc-containing particulate composite hydrotalcite as an effective component that has an excellent effect for treating the ulcer.

BACKGROUND ART

Agents for treating ulcer have long been studied, and a numerous kinds of products have been developed. Peptic ulcer is caused by a high acidity of acid in the stomach, accelerated excitation of autonomic nerve, interruption in blood circulation in the walls of the stomach, stress, etc. As the anti-ulcerating agents, there have been used a mucous membrane-protecting agent and an aggressive factor inhibitor for inhibiting the secretion of acid in the stomach, such as $H_2$ blocker and proton pump inhibitor. As the modern anti-ulcerating agents, there have been known an $H_2$ blocker containing decreased numbers of granules and a proton pump inhibitor that inhibits the formation of granular super-oxide (non-patent document 1). In recent years, further, attention has been given to the wound-healing action of zinc (Zn), and an agent for treating the ulcer has been developed by blending an organic material with zinc (Zn). For example, there have been developed a histamine $H_2$ acceptor by utilizing such a feature that a complex of zinc (Zn) can be easily incorporated, as well as a cimetidine/zinc complex obtained by blending the cimetidine of an antagonist with zinc (patent document 1).

Most of these agents for treating the ulcer are organic materials which may affect the safety of the human bodies.

As the inorganic agent for treating the ulcer, there have been used synthetic particulate hydrotalcites which are gastric antacids (patent document 2 and patent document 3). It has been said that the synthetic particulate hydrotalcites are ideal medicinal gastric antacids.

The synthetic particulate hydrotalcite that is a gastric antacid is also effective as an agent for treating the ulcer, and its preparation method has been disclosed in U.S. patent specifications (patent document 4 and patent document 5). The particulate hydrotalcite is typically represented by a chemical formula $Mg_6Al_2(OH)_{16}CO_3.4H_2O$. When used as the agent for treating the ulcer, however, the conventional particulate hydrotalcite must be internally used for extended periods of time often causing damage to the mucous membrane of the internal walls of the stomach.

[Non-patent document 1] Digestive Diseases and Sciences, Vol. 45, No. 9, pp. 1786-1791 (September, 2000)
[Patent document 1] JP-A-6-49035
[Patent document 2] JP-B-46-2280
[Patent document 3] JP-B-50-30039
[Patent document 4] U.S. Pat. No. 3,539,306
[Patent document 5] U.S. Pat. No. 3,650,704

DISCLOSURE OF THE INVENTION

Problems to be Solved by the Invention

The particulate hydrotalcite serves as an excellent agent for treating the ulcer but must be internally used for extended periods of time often causing damage to the mucous membrane of the internal walls of stomach after internally used for extended periods of time. Therefore, a further improvement is desired from the standpoint of protecting the internal walls of the stomach. It is therefore an object of the present invention to provide an improved particulate composite hydrotalcite effective for use as an agent for treating ulcer having excellent effect for treating the ulcer when internally used even for short periods of time without damaging the mucous membrane of the internal walls of the stomach.

Means for Solving the Problems

The present inventors have forwarded the study to improve the particulate hydrotalcite in an attempt to achieve the above object. As a result, the inventors have discovered that a particulate composite hydrotalcite comprising the particulate hydrotalcite which contains zinc (Zn) in a very small and particular amount as a solid solution exhibits excellent action for treating the ulcer without damaging the mucous membrane of the internal walls of the stomach. Namely, it was discovered that there can be provided a particulate composite hydrotalcite which is an agent for treating the ulcer offering immediate effect without side effects as compared to the conventional agents for treating the ulcer.

The particulate composite hydrotalcite of the invention contains zinc in a predetermined amount as a solid solution. The particulate composite hydrotalcite is a compound in which zinc is substituted for part of magnesium in the conventional particulate hydrotalcite that does not contain zinc. Due to zinc contained as a solid solution, the particulate composite hydrotalcite achieves the effect for treating the ulcer. This fact will become obvious from Comparative Examples described later. In Comparative Examples described later, the particulate hydrotalcite ($Mg_6Al_2(OH)_{16}.CO_3.4H_2O$) without containing zinc was blended with zinc oxide (ZnO), and was orally administered. However, the therapeutic effect due to the zinc oxide (ZnO) was not virtually recognized.

In the case of the stomach ulcer due to excess of stress, the zinc (Zn) concentration in the blood decreases due to stress. This is because a protein called metallothionine is formed in large amounts in the liver due to stress using, however, zinc in large amounts. Therefore, zinc (Zn) in the blood collects in the liver, and the zinc concentration in the blood decreases and cannot be sufficiently supplied to the stomach. This results in a decrease in the concentration of zinc in the blood that suppresses the occurrence of ulcer. It is considered that the particulate composite hydrotalcite of the invention that is internally used not only heals the wound in the mucous membrane of the internal walls of the stomach but also is decomposed in the stomach due to acid in the stomach, enabling zinc (Zn) to be effectively absorbed by the blood, contributing to increasing the zinc (Zn) concentration in the liver and in the blood, so that zinc (Zn) is supplied to the stomach to assist the healing of the ulcer.

The particulate composite hydrotalcite of the invention, further, works to supply zinc which is one of the minerals essential for the human body. Zinc which is one of the essential minerals tends to become in short supply in recent years.

Shortage of zinc decreases the sense of taste or immunity. In the case of pregnant women, in particular, zinc in the body migrates to the fetus, causing the shortage of zinc and decreased immunity. It has also been reported that the shortage of zinc induces depression. If a baby is born lacking zinc, brain waves of a depressive state are often observed from the baby, and it has now been learned that proteins for forming brain cells are not synthesized, adversely affecting the learning and memorizing abilities. Anemia due to zinc deficiency has also been reported. There is also a report that about 48% of anemic women were suffering from the zinc deficiency.

A very small amount of zinc that is liable to be in short supply in the human body can be provided by a particulate composite hydrotalcite obtained by solidly dissolving zinc in the particulate hydrotalcite. It can, therefore, be said that the particulate composite hydrotalcite of the invention is a novel agent for treating the ulcer having both the effect for treating the peptic ulcer and the effect for supplying zinc.

Namely, the present inventors have discovered that the particulate composite hydrotalcite obtained by solidly dissolving a very small amount of zinc ions, which are relatively inexpensive and non-toxic or relatively lowly toxic, in the particulate hydrotalcite, is very effective in treating the stomach ulcer and is also effective in supplying zinc (Zn) as a mineral, and have thus arrived at the present invention.

According to the present invention, there are provided the following agent for treating ulcer and the use thereof.

(1) An agent for treating ulcer containing a particulate composite hydrotalcite represented by the following formula (1) as an effective component,

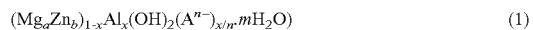  (1)

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4, 0.1 \leq a < 1, 0 < b \leq 0.5, 0 \leq m < 1$.

(2) The agent for treating ulcer as described in (1) above, wherein $A^{n-}$ in the formula (1) is $CO_3^{2-}$ or $SO_4^{2-}$.
(3) The agent for treating ulcer as described in (1) above, wherein $A^{n-}$ in the formula (1) is $CO_3^{2-}$.
(4) The agent for treating ulcer as described in (1) above, wherein x in the formula (1) satisfies $0.2 \leq x \leq 0.35$.
(5) The agent for treating ulcer as described in (1) above, wherein b in the formula (1) satisfies $0.0005 \leq b \leq 0.2$.
(6) The agent for treating ulcer as described in (1) above, wherein b in the formula (1) satisfies $0.005 \leq b \leq 0.1$.
(7) The agent for treating ulcer as described in (1) above, wherein a in the formula (1) satisfies $0.2 \leq a \leq 0.9$.
(8) The agent for treating ulcer as described in (1) above for treating the peptic ulcer in mammals.
(9) The agent for treating ulcer as described in (1) above for treating the peptic ulcer in humans.
(10) The agent for treating ulcer as described in (1) above for treating the stomach ulcer or the duodenal ulcer in humans.
(11) Use of the particulate composite hydrotalcite as described in (1) above for treating the ulcer.
(12) The agent for treating ulcer as described in (1) above in a form that can be orally administered.
(13) A tablet for treating ulcer containing the particulate composite hydrotalcite as described in (1) above as an effective component.
(14) A granular agent or a fine granular agent containing the particulate composite hydrotalcite as described in (1) above as an effective component.
(15) A slurry agent for treating ulcer containing the particulate composite hydrotalcite as described in (1) above as an effective component.
(16) A zinc-supplying agent containing the particulate composite hydrotalcite as described in (1) above as an effective component.
(17) A method of treating peptic ulcer by orally administering an effective amount of the particulate composite hydrotalcite as described in (1) above to a person suffering from the peptic ulcer.
(18) Use of the particulate composite hydrotalcite as described in (1) above for preparing a medicine for the treatment of ulcer.

Effect of the Invention

According to the present invention, there is provided a particulate composite hydrotalcite having an effect for treating the peptic ulcer. The particulate composite hydrotalcite is a particulate synthetic hydrotalcite that contains a predetermined amount of zinc (Zn) as a solid solution, and is represented by the above formula (1). When orally administered, the particulate composite hydrotalcite works to quickly heal the peptic ulcer. The healing effect is exhibited more immediately than the particulate hydrotalcite that does not contain zinc, side effects are small, and very little damages are caused to the mucous membrane of the internal walls of the stomach and to the intestines.

BEST MODE FOR CARRYING OUT THE INVENTION

As descried above, the particulate composite hydrotalcite of the invention is represented by the following formula (1),

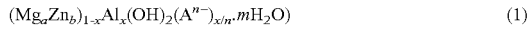  (1)

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4, 0.1 \leq a < 1, 0 < b \leq 0.5, 0 \leq m < 1$.

The particulate composite hydrotalcite of the present invention represented by the formula (1) is a particulate hydrotalcite containing a small amount of zinc (Zn) as a solid solution. Therefore, the particulate composite hydrotalcite of the present invention is a compound having the same crystalline structure as that of the particulate hydrotalcite, and exhibits the same diffraction pattern as that of the particulate hydrotalcite as measured by the powder X-ray diffraction method (see Table 1). Further, the particulate composite hydrotalcite of the present invention contains zinc that is solidly dissolved in the hydrotalcite and does not damage the internal walls of the stomach or the internal walls of the intestines even when it is orally administered.

The particulate composite hydrotalcite of the present invention has a chemical structure represented by the above formula (1). The formula (1) will now be concretely described. In the formula (1), $A^{n-}$ is an anion having a valency of n, and is $CO_3^{2-}$, $SO_4^{2-}$ or $Cl^-$, and is, preferably, $CO_3^{2-}$ or $SO_4^{2-}$, and is, most preferably, $CO_3^{2-}$. These anions may include two kinds, e.g., $CO_3^{2-}$ and $SO_4^{2-}$, simultaneously. Here, x satisfies $0.18 \leq x \leq 0.4$ and is, preferably, $0.2 \leq x \leq 0.35$ and, more preferably, $0.24 \leq x \leq 0.3$. Further, b satisfies $0 < b \leq 0.5$ and is, preferably, $0.0005 \leq b \leq 0.2$ and, particularly preferably, $0.005 \leq b \leq 0.1$. Further, a satisfies $0.1 \leq a < 1$, and, more preferably, $0.2 \leq a \leq 0.9$ and, particularly, $0.3 \leq a \leq 0.8$. Further, m stands for the content of crystal water and satisfies $0 \leq m < 1$ and, preferably, $0.1 \leq m < 1$.

The particulate composite hydrotalcite of the present invention is almost nontoxic, and its $LD_{50}$ is larger than 15,000 mg/kg (orally, rat).

The method of producing the particulate composite hydrotalcite of the present invention is basically the same as the known method of producing the particulate hydrotalcite (e.g., U.S. Pat. No. 3,539,306). Here, zinc (Zn) is added to the starting material together with a magnesium salt and/or an aluminum salt so as to be contained therein as a solid solution. Zinc (Zn) should be added in a predetermined amount to the starting material, preferably, in the form of a water-soluble salt such as nitrate, sulfate or chloride, and the reaction conditions are selected from those in a range described in the above U.S. patent.

The method of producing the particulate composite hydrotalcite of the present invention comprises bringing an aqueous solution containing, for example, salts of Mg, Zn and Al (nitrate, chloride and sulfate) at ratios of metal elements that constitute the desired particulate hydrotalcite, an aqueous solution of sodium carbonate ($Na_2CO_3/Al=0.35$ to 0.75) and an aqueous solution of sodium hydroxide into contact with each other, so as to be co-precipitated while holding the pH of the reaction solution at 10 to 10.5 with the aqueous solution of sodium hydroxide. The reaction is conducted at room temperature to 100° C. The reaction product can be used in its form or may be washed, and the suspension thereof (aqueous system) may be subjected to the hydrothermal reaction at a temperature of 70 to 200° C. for 0.5 to 24 hours.

Though there is no particular limitation on the shape of the particulate composite hydrotalcite of the present invention, it is advantageous if the particles have an average secondary particle size of 0.1 to 20 μm and, preferably, 0.2 to 10 μm as measured by the laser diffraction scattering method, and it is desired that particles have a BET specific surface area of 5 to 30 m²/g and, preferably, 7 to 25 m²/g.

When used as an agent for treating ulcer, the particulate composite hydrotalcite of the invention can be used in any form such as powder, fine granule, granule, tablet, capsule or slurry, and, as required, there can be added a vehicle, a bonding agent, a disintegrant and a lubricant thereto.

As the bonding agent, there can be used crystalline cellulose or starches. As the disintegrant, there can be used starch-type disintegrants such as corn starch, potato starch, dextrin, hydroxypropyl starch, starch partly in α-form, and carboxymethyl starch sodium, as well as croscarmellose sodium, carmellose calcium, carmellose and carboxystarch sodium.

When the particulate composite hydrotalcite of the invention is to be formed as tablets, the particulate composite hydrotalcite is contained advantageously in an amount of 70 to 99.5% by weight and, preferably, 80 to 99% by weight per the whole weight of the tablets. Further, the tablets can contain additives in amounts of 0.1 to 30% by weight, preferably, 0.5 to 20% by weight. As the additives in the tablets, there can be exemplified the above-mentioned bonding agent and disintegrant, as well as sweetening agent, taste moderator, perfume, lubricant, coloring agent and coating agent. The tablets can be formed in such a shape as round shape, oval shape, spherical shape, doughnut shape or rod-like shape.

The agent for treating ulcer of the invention is effective in restoring the tissues, such as healing various kinds of ulcers in mammals. The agent for treating ulcer of the invention is particularly effective in treating the peptic ulcer. That is, the treating agent of the invention exhibits an immediate effect in recovering the ulcer in the digestive organs such as oral cavity, gullet, stomach, duodenum, small intestine and large intestine. In particular, the treating agent of the invention exhibits distinguished therapeutic effect for the ulcers in the stomach and duodenum. The reason is because the particulate composite hydrotalcite contained in the treating agent of the invention by itself is an excellent gastric antacid, exhibiting immediate effect for neutralizing the pH of the acid in the stomach and sustaining the neutralizing effect, presumably contributing to heating the ulcer.

The agent for treating ulcer of the invention is effective for various animals if they are mammals. The agent for treating ulcer is effective not only for humans but also for domestic animals such as cattle, pigs, sheep and the like, as well as for pets such as dogs, cats and the like. In particular, the agent for treating ulcer exhibits excellent effect for treating the peptic ulcer (especially, the stomach ulcer and the duodenal ulcer) of humans.

When orally administered, the agent for treating ulcer of the invention is administered in an amount, as the particulate composite hydrotalcite, in a range of 0.2 to 5 g and, preferably, 1 to 4 g per an adult a day.

Depending upon the symptoms, however, the amount of administration may increase or decrease beyond the above range.

The invention will now be described in detail by way of Examples.

In Examples, (a) analytical methods of Zn and As of the particulate composite hydrotalcite, (b) average secondary particle size, (c) BET specific surface area and (d) X-ray diffraction, all stand for values measured by the methods described below.

(a) Analysis of Zn and As (Arsenic).
  Measured by the atomic absorption method.

(b) Average Secondary Particle Size.
  Measured by the laser diffraction scattering method.
  Measured by using the MICROTRACK particle size profile meter (X-100 HRA, manufactured by Nikkiso Co.).
  70 Milliliters of a solution of sodium hexametaphosphate of 0.2 W/V % was gradually added to 700 mg of a sample powder and was dispersed with ultrasonic waves for 3 minutes by using an ultrasonic homogenizer, US-330T, manufactured by Nihon Seiki Seisakusho Co. After dispersed with ultrasonic waves, the dispersion solution was immediately stirred by using a mini-stirrer. Within one minute after the treatment with ultrasonic waves, 2.5 to 4.0 mL of the dispersion solution was picked up and was added to a solvent circulator of the MICROTRACK particle size profile meter (X-100 HRA, manufactured by Nikkiso Co.) and, after one minute has passed, was measured for its particle size profile. Measurement was taken a total of two times, and an arithmetic mean value of 50% cumulative secondary particle sizes obtained through the measurement was calculated to regard it as an average secondary particle size of the sample.

(c) BET Specific Surface Area.
  Measured by the adsorption method using liquid nitrogen.

(d) Powder X-Ray Diffraction Measuring Method.
  $CuK_\alpha$ angle (2θ): 5 to 65°, step; 0.02,
  scan speed; 4°/min, control voltage; 40 KV,
  control current; 20 mA,
  apparatus; RINT 2200VX diffraction system (manufactured by Rigaku Denki Co.).

EXAMPLE 1

A mixed aqueous solution {referred to as solution A} of magnesium nitrate of a concentration of 1.50 mols/L, zinc nitrate of a concentration of $3.61 \times 10^{-3}$ mols/L and aluminum nitrate of a concentration of 0.752 mols/L, an aqueous solution {solution B} of sodium carbonate of a concentration of 0.45 mols/L, and an aqueous solution {solution C} of sodium hydroxide of a concentration of 3.4 N were prepared. Next, by using a metering pump, the solution A, the solution B and the solution C were poured into a reaction vessel at such flow rates that the volume ratio of the solution A and the solution B was 1 and 1, and the pH value of the reaction solution was adjusted with the solution C so as to be maintained in a range of 10 to 10.5, and the reaction was carried out at a temperature of 40° C. to form a precipitate. The precipitate was filtered, washed, dried overnight at 110° C., pulverized and was sieved to obtain a particulate composite hydrotalcite of the following composition. The washing consisted of washing with water and, then with hydrochloric acid of $10^{-3}$ mols/L. The amount of hydrochloric acid at this moment was 30 times as great as the weight of the particulate composite hydrotalcite.

Composition: $Mg_{0.665}Zn_{0.0016}Al_{0.333}(OH)_2(CO_3)_{0.167} \cdot 0.5H_2O$ The analytical result of Zn in the particulate composite hydrotalcite was as shown in Table 2. Table 2 also shows the analytical result of arsenic (As) (the same holds hereinafter).

EXAMPLE 2

A mixed aqueous solution {referred to as solution A} of magnesium nitrate of a concentration of 1.20 mols/L, zinc nitrate of a concentration of 0.754 mols/L and aluminum nitrate of a concentration of 0.31 mols/L, an aqueous solution {solution B} of sodium carbonate of a concentration of 0.45 mols/L, and an aqueous solution {solution C} of sodium hydroxide of a concentration of 3.4 N were prepared. Next, the reaction was conducted by the same method as that of Example 1 to obtain a particulate composite hydrotalcite of the following composition.

Washing was conducted by using water and, then an aqueous solution of nitric acid of $10^{-4}$ mol/L in an amount 30 times as great as the weight of the particulate composite hydrotalcite.

Composition: $Mg_{0.53}Zn_{0.137}Al_{0.333}(OH)_2(CO_3)_{0.167} \cdot 0.5H_2O$

The analytical result of Zn in the particulate composite hydrotalcite was as shown in Table 2.

EXAMPLE 3

A mixed aqueous solution {solution A} of magnesium nitrate of a concentration of 1.50 mols/L, zinc nitrate of a concentration of $3.08 \times 10^{-3}$ mols/L and aluminum nitrate of a concentration of 0.501 mols/L, an aqueous solution {solution B} of sodium carbonate of a concentration of 0.30 mols/L, and an aqueous solution {solution C} of sodium hydroxide of a concentration of 3.4 N were prepared. Next, the reaction was carried out in the same manner as in Example 1 to obtain a particulate composite hydrotalcite of the following composition. The washing consisted of washing with water and, then with acetic acid of $10^{-3}$ mols/L in an amount 30 times as great as the weight of the particulate composite hydrotalcite.

Composition: $Mg_{0.7485}Zn_{0.0015}Al_{0.25}(OH)_2(CO_3)_{0.125} \cdot 0.5H_2O$ The analytical result of Zn in the particulate composite hydrotalcite was as shown in Table 2.

EXAMPLE 4

A mixed aqueous solution {solution A} of magnesium nitrate of a concentration of 1.50 mols/L, zinc nitrate of a concentration of $1.733 \times 10^{-2}$ mols/L and aluminum nitrate of a concentration of 0.506 mols/L, an aqueous solution {solution B} of sodium carbonate of a concentration of 0.304 mols/L, and an aqueous solution {solution C} of sodium hydroxide of a concentration of 3.4 N were prepared. Next, the reaction was carried out in the same manner as in Example 1, and the obtained reaction solution was hydrothermally reacted at 150° C. for 12 hours. After cooled, the reaction product was filtered, washed with water, washed with an aqueous solution (0.03 mols) of sodium carbonate of 0.1 mol/L and was, further, washed with water. Next, the reaction product was washed with hydrochloric acid of $10^{-4}$ mols/L in an amount 40 times as great as the weight of the particulate composite hydrotalcite. The reaction product was dried overnight at 110° C., pulverized and sieved to obtain a particulate composite hydrotalcite of the following composition.

Composition: $Mg_{0.7414}Zn_{0.0086}Al_{0.25}(OH)_2(CO_3)_{0.125} \cdot 0.5H_2O$ The analytical result of Zn in the particulate composite hydrotalcite was as shown in Table 2.

EXAMPLE 5

A mixed aqueous solution {solution A} of magnesium sulfate of a concentration of 1.50 mols/L, zinc sulfate of a concentration of $2.9 \times 10^{-3}$ mols/L and aluminum sulfate of a concentration of 0.1879 mols/L, an aqueous solution {solution B} of sodium carbonate of a concentration of 0.23 mols/L, and an aqueous solution {solution C} of sodium hydroxide of a concentration of 3.4 N were prepared. Next, the reaction was carried out in the same manner as in Example 1, and the obtained reaction solution was filtered, washed with water, washed with an aqueous solution of sodium carbonate of a concentration of 0.1 mol/L and was, further, washed with water. Next, the reaction solution was washed with hydrochloric acid of $10^{-4}$ mols/L in an amount 40 times as great as the weight of the particulate composite hydrotalcite. The reaction product was dried overnight at 40° C., pulverized and sieved to obtain a particulate composite hydrotalcite of the following composition.

Composition: $Mg_{0.7985}Zn_{0.0015}Al_{0.20}(OH)_2(CO_3)_{0.0994}(SO_4)_{0.0006} \cdot 0.75H_2O$ The analytical result of Zn in the particulate composite hydrotalcite was as shown in Table 2.

EXAMPLE 6

A mixed aqueous solution {solution A} of magnesium sulfate of a concentration of 1.50 mols/L, zinc sulfate of a concentration of $1.627 \times 10^{-2}$ mols/L and aluminum sulfate of a concentration of 0.1895 mols/L, an aqueous solution {solution B} of sodium carbonate of a concentration of 0.23 mols/L, and an aqueous solution {solution C} of sodium hydroxide of a concentration of 3.4 N were prepared. Next, the reaction was carried out in the same manner as in Example 1, and the obtained reaction solution was filtered, washed with water, washed with an aqueous solution of sodium carbonate of a concentration of 0.1 mol/L and was, further, washed with water. Next, the reaction solution was washed with acetic acid of $10^{-4}$ mols/L in an amount 40 times as great as the weight of the particulate composite hydrotalcite. The reaction product was dried overnight at 110° C., pulverized and sieved to obtain a particulate composite hydrotalcite of the following composition.

Composition: $Mg_{0.7914}Zn_{0.0086}Al_{0.20}(OH)_2(CO_3)_{0.0994}(SO_4)_{0.0006} \cdot 0.6H_2O$ The analytical result of Zn in the particulate composite hydrotalcite was as shown in Table 2.

EXAMPLE 7

A mixed aqueous solution {solution A} of magnesium chloride of a concentration of 1.50 mols/L, zinc sulfate of a concentration of $2.03 \times 10^{-2}$ mols/L and aluminum chloride of a concentration of 0.507 mols/L, an aqueous solution {solution B} of sodium carbonate of a concentration of 0.30 mols/L, and an aqueous solution {solution C} of sodium hydroxide of a concentration of 3.4 N were prepared. Next, the reaction was carried out in the same manner as in Example 1 to obtain a particulate composite hydrotalcite of the following composition. Washing was conducted by using water and, then nitric acid of $10^{-4}$ mol/L in an amount 40 times as great as the weight of the particulate composite hydrotalcite.

Composition: $Mg_{0.74}Zn_{0.01}Al_{0.25}(OH)_2(CO_3)_{0.125} \cdot 0.5H_2O$

The analytical result of Zn in the particulate composite hydrotalcite was as shown in Table 2. Further, Table 1 shows characteristic peaks in a diffraction pattern of the particulate composite hydrotalcite as measured by the powder X-ray diffraction method.

EXAMPLE 8

A mixed aqueous solution {solution A} of magnesium chloride of a concentration of 1.20 mols/L, zinc sulfate of a concentration of $1.13 \times 10^{-2}$ mols/L and aluminum chloride of a concentration of 0.404 mols/L, an aqueous solution {solution B} of sodium carbonate of a concentration of 0.24 mols/L, and an aqueous solution {solution C} of sodium hydroxide of a concentration of 3.4 N were prepared. Next, the reaction was carried out in the same manner as in Example 1, and the obtained reaction solution was washed, and the suspension thereof (aqueous system) was hydrothermally reacted at 120° C. for 15 hours. After cooled, the reaction product was filtered, washed, dried overnight at 110° C., pulverized and sieved to obtain a particulate composite hydrotalcite of the following composition. Washing was conducted by using water and, then acetic acid of $10^{-4}$ mol/L in an amount 40 times as great as the weight of the particulate composite hydrotalcite.

Composition: $Mg_{0.743}Zn_{0.007}Al_{0.25}(OH)_2(CO_3)_{0.125} \cdot 0.5H_2O$

The analytical result of Zn in the particulate composite hydrotalcite was as shown in Table 2.

EXAMPLE 9

290 Milliliters of a mixed aqueous solution {solution A} of magnesium chloride of a concentration of 1.20 mols/L, zinc nitrate of a concentration of $4.82 \times 10^{-3}$ mols/L and aluminum sulfate of a concentration of 0.20 mols/L, and a mixed aqueous solution {solution B} of 273 ml of an aqueous solution of sodium hydroxide of a concentration of 3.4 mols/L and 290 ml of an aqueous solution of sodium carbonate of a concentration of 0.24 mols/L, were prepared.

Next, the solution B was introduced into a one-liter container and to which the solution A was added at room temperature with stirring. After stirred for another 40 minutes, the reaction solution was hydrothermally reacted at 150° C. for 8 hours. After cooled, the reaction product was filtered, washed with water, further, washed with sodium carbonate (0.03 mols/L) of a concentration of 0.078 mols/L, further, washed with water, and was dried overnight at 105° C. The reaction product was pulverized and sieved to obtain a particulate composite hydrotalcite of the following composition.

Composition: $Mg_{0.747}Zn_{0.003}Al_{0.25}(OH)_2(CO_3)_{0.125} \cdot 0.5H_2O$

The analytical result of Zn in the particulate composite hydrotalcite was as shown in Table 2.

The particulate composite hydrotalcite was measured for its contents of lead (Pb), cadmium (Cd) and chromium (Cr) by the atomic absorption method to be not larger than 0.1 ppm, 0.23 ppm and 0.69 ppm, respectively, and was measured for its content of mercury (Hg) by the reduction-vaporized atomic absorption method to be not larger than 0.01 ppm. Further, the contents of sulfuric acid ions ($SO_4$) and chlorine ions (Cl) were measured by the fluorescence X-ray method to be 0.077% by weight and 0.007% by weight, respectively.

EXAMPLE 10

A mixed aqueous solution {solution A} of magnesium chloride of a concentration of 1.20 mols/L, zinc nitrate of a concentration of $7.21 \times 10^{-3}$ mols/L and aluminum chloride of a concentration of 0.604 mols/L, an aqueous solution {solution B} of sodium carbonate of a concentration of 0.36 mols/L, and an aqueous solution {solution C} of sodium hydroxide of a concentration of 3.4 N were prepared. Next, the reaction was carried out in the same manner as in Example 1, and the obtained reaction solution was heated and reacted at 90° C. for 8 hours. After cooled, the reaction product was filtered, washed, dried overnight at 110° C., pulverized and sieved to obtain a particulate composite hydrotalcite of the following composition. Washing was conducted by using water and, then nitric acid of $10^{-5}$ mol/L in an amount 50 times as great as the weight of the particulate composite hydrotalcite.

Composition: $Mg_{0.662}Zn_{0.004}Al_{0.333}(OH)_2(CO_3)_{0.167} \cdot 0.5H_2O$

The analytical result of Zn in the particulate composite hydrotalcite was as shown in Table 2.

EXAMPLE 11

A mixed aqueous solution {solution A} of magnesium chloride of a concentration of 1.20 mols/L, zinc nitrate of a concentration of $1.09 \times 10^{-2}$ mols/L and aluminum chloride of a concentration of 0.605 mols/L, an aqueous solution {solution B} of sodium carbonate of a concentration of 0.36 mols/L, and an aqueous solution {solution C} of sodium hydroxide of a concentration of 3.4 N were prepared. Next, the reaction was carried out in the same manner as in Example 1, the obtained reaction solution was washed, and the suspension thereof (aqueous system) was hydrothermally reacted at 130° C. for 4 hours. After cooled, the reaction product was filtered, washed, dried overnight at 110° C. and pulverized to obtain a particulate composite hydrotalcite of the following composition. Washing was conducted by using water and, then acetic acid of $10^{-5}$ mol/L in an amount 50 times as great as the weight of the particulate composite hydrotalcite.

Composition: $Mg_{0.660}Zn_{0.006}Al_{0.333}(OH)_2(CO_3)_{0.167} \cdot 0.5H_2O$

The analytical result of Zn was as shown in Table 2.

EXAMPLE 12

273 Milliliters of an aqueous solution of sodium hydroxide of 3.4 N and 58 ml of an aqueous solution of sodium carbonate of 1.2 mols/L were introduced into a one-liter container and to which was added a mixed aqueous solution of 284 ml of an aqueous solution of aluminum chloride of 1.2 mols/L, 10 ml of an aqueous solution of zinc nitrate of 0.7 mols/L and 58 ml of an aqueous solution of aluminum sulfate of 1 mol/L at room temperature with stirring. After stirred for one hour, the mixture was transferred into an autoclave, and was hydrothermally reacted at 150° C. for 12 hours. After cooled, the hydrothermally reacted product was filtered, washed with water, washed with 400 ml (0.03 mols) of an aqueous solution of sodium carbonate, washed with water, and was dried overnight at 110° C. Thereafter, the reaction product was pulverized and sieved to obtain a particulate composite hydrotalcite of the following composition.

Composition: $Mg_{0.735}Zn_{0.015}Al_{0.25}(OH)_2(CO_3)_{0.125} \cdot 0.5H_2O$

The analytical result of Zn in the particulate composite hydrotalcite was as shown in Table 2.

EXAMPLE 13

A mixed aqueous solution {solution A} of magnesium chloride of a concentration of 1.5 mols/L, zinc nitrate of a concentration of 0.23 mols/L and aluminum sulfate of a concentration of 0.288 mols/L, an aqueous solution {solution B} of sodium carbonate of a concentration of 0.346 mols/L, and an aqueous solution {solution C} of sodium hydroxide of a concentration of 3.4 N were prepared. Next, by using a metering pump, the solution A and the solution B were poured at the same flow rate into a reaction vessel into which de-ionized water has been introduced, and the pH value of the reaction solution was adjusted with the solution C so as to be maintained in a range of 10 to 10.5 to form a precipitate. The reaction temperature was 40° C. and the residence time of the reaction solution in the reaction vessel was 40 minutes. The precipitate was filtered, washed, dried overnight at 110° C., pulverized and was sieved to obtain a particulate composite hydrotalcite of the following composition.

Composition: $Mg_{0.65}Zn_{0.1}Al_{0.25}(OH)_2(CO_3)_{0.125} \cdot 0.5H_2O$

The analytical result of Zn in the particulate composite hydrotalcite was as shown in Table 2.

EXAMPLE 14

2.82 Liters of an aqueous solution of magnesium sulfate of 1.4 mols/L, one liter of an aqueous solution of aluminum sulfate of 1 mol/L, and 0.1 liter of an aqueous solution of zinc chloride of 1.0 mol/L were introduced into a 5-liter plastic beaker, and were stirred well to prepare an Mg—Al—Zn mixed solution {solution A}. 4 Liters of an aqueous solution of sodium hydroxide of 3.0 mols/L was introduced into a 10-liter stainless steel round vessel and into which the solution A was thrown with stirring over 60 minutes by using a metering pump. The obtained reaction suspension was filtered, washed, dried and was pulverized by using a Laboscale mill to obtain a particulate composite hydrotalcite of the following composition. The reaction temperature was 28 to 32° C., and the pH of the solution at the end of the reaction was 10.6.

Composition: $Mg_{0.658}Zn_{0.017}Al_{0.333}(OH)_2(SO_4)_{0.175} \cdot 0.398H_2O$ The analytical result of Zn in the particulate composite hydrotalcite was as shown in Table 2.

EXAMPLE 15

A mixed aqueous solution {solution A} of magnesium chloride of a concentration of 0.2 mols/L, zinc nitrate of 0.6 mols/L and aluminum sulfate of 0.2 mols/L, an aqueous solution {solution B} of sodium carbonate of 0.24 mols/L, and an aqueous solution {solution C} of sodium hydroxide of 3.4 N were prepared. Next, by using the metering pump, the solution A and the solution B were poured at the same flow rate into the reaction vessel into which de-ionized water has been introduced, and the pH value of the reaction solution was adjusted with the solution C so as to be maintained in a range of 9.0 to 9.5 to form a precipitate. The reaction temperature was 35° C. and the residence time of the reaction solution in the reaction vessel was 30 minutes. The precipitate was filtered, washed, dried overnight at 110° C., pulverized and was sieved to obtain a particulate composite hydrotalcite of the following composition.

Composition: $Mg_{0.167}Zn_{0.5}Al_{0.333}(OH)_2(CO_3)_{0.167} \cdot 0.5H_2O$

The analytical result of Zn in the particulate composite hydrotalcite was as shown in Table 2.

EXAMPLE 16

(1) Preparation of an aluminum hydroxide suspension.

As a dry aluminum hydroxide gel that complies with the Revised Regulation 15, Japanese Pharmacopoeia, 47 g of S-100, trade name ($Al_2O_3$ content, 54%) manufactured by Kyowa Kagaku Kogyo Co. was used being suspended in 150 mL of tap water.

(2) Method of reaction.

500 Milliliters of tap water and 3.8 g of zinc chloride ($ZnCl_2$), special grade chemical, manufactured by Wako Junyaku Kogyo Co., were thrown into a 2-liter beaker with stirring so as to be dissolved. Thereafter, 140 g of basic magnesium carbonate of the shape of strips (trade name, Shita) manufactured by Kyowa Kagaku Kogyo Co. was thrown therein, the suspension of the aluminum hydroxide gel described in (1) above was thrown therein and, further, 598 mL of an aqueous solution of sodium hydroxide of 3.3 mols/L was added thereto. Thereafter, the liquid temperature was elevated to 90° C., and the mixture was ripened at this temperature for 3 hours. After cooled, the obtained reaction suspension was washed by using the Buchner funnel under reduced pressure, dehydrated, dried at 90° C. for 20 hours, and was pulverized by using the Laboscale hammer mill to obtain a particulate composite hydrotalcite of the following composition. The pH of the reaction suspension after the end of the ripening was 10.73.

Composition: $Mg_{0.732}Zn_{0.013}Al_{0.25}(OH)_2(CO_3)_{0.171} \cdot 0.6H_2O$

The analytical result of Zn in the particulate composite hydrotalcite was as shown in Table 2. Further, the obtained particulate composite hydrotalcite was observed through a microscope to learn that the particles were of a pole-like shape having a long axis of 23 to 62 μm in length and a short axis of 7 to 12 μm in length.

TABLE 1

X-Ray diffraction.
The sample is the particulate composite hydrotalcite of Example 7.

| Peak No. | 2θ | D-Value | Relative intensity |
|---|---|---|---|
| 1 | 11.320 | 7.8102 | 100 |
| 2 | 22.820 | 3.8937 | 52 |
| 3 | 34.420 | 2.6034 | 14 |
| 4 | 38.320 | 2.3469 | 7 |
| 5 | 39.880 | 2.2587 | 4 |
| 6 | 45.140 | 2.0069 | 5 |
| 7 | 46.680 | 1.9442 | 4 |
| 8 | 60.420 | 1.5309 | 12 |
| 9 | 61.700 | 1.5021 | 14 |

TABLE 2

| Example | Zn (wt %) | As (ppm) |
|---|---|---|
| 1 | 0.15 | 0.2 |
| 2 | 10.7 | 0.1 |
| 3 | 0.13 | 0.5 |
| 4 | 0.74 | 0.3 |
| 5 | 0.12 | 0.1 |
| 6 | 0.74 | 0.1 |
| 7 | 0.86 | 0.1 |
| 8 | 0.60 | 0.2 |
| 9 | 0.25 | 0.1 |
| 10 | 0.33 | 0.1 |
| 11 | 0.50 | 0.1 |
| 12 | 1.15 | 0.2 |
| 13 | 8.2 | 0.1 |
| 14 | 1.3 | 0.3 |
| 15 | 33 | 0.1 |
| 16 | 1.02 | 0.5 |
| Comp. Ex. 1 | — | 0.1 |

COMPARATIVE EXAMPLE 1

A particulate hydrotalcite (trade name: ALCAMAC) manufactured by Kyowa Kagaku Kogyo Co. was used. The "ALCAMAC" was a particulate hydrotalcite represented by a chemical formula, $Mg_6Al_2(OH)_{16}(CO_3) \cdot 4H_2O$. The ALCAMAC was measured for lead (Pb), cadmium (Cd), chromium (Cr), mercury (Hg), sulfuric acid ions ($SO_4$) and chlorine ions (Cl) in the same manner as in Example 9 to be 0.1 ppm>, 0.20 ppm, 0.72 ppm, 0.01 ppm>, 0.090 wt % and 0.010 wt %, respectively.

COMPARATIVE EXAMPLE 2

Preparation of a mixed sample of the particulate hydrotalcite and particulate zinc oxide:

2.83 Grams of zinc oxide (ZnO), Japanese Pharmacopoeia, was added to 1.5 L of a slurry of 150 g/L of particulate hydrotalcite (ALCAMAC, trade name of Kyowa Kagaku Co.) so that the amount of Zn was 1% by weight, mixed together so as to become uniform, and the mixture thereof was spray-dried by using a spray drier to obtain a mixed sample. An X-ray micro-analyzer (EPMA manufactured by Nihon Denshi Co.) was used to make sure if the mixture was uniformly dispersed.

EXAMPLE 17

Pharmacological test.

Effect upon the stomach ulcer was examined by using male rats (SPF) and the particulate composite hydrotalcite obtained in Example 12. As the particulate hydrotalcite, there was used the "ALCAMAC", trade name, manufactured by Kyowa Kagaku Kogyo Co. The "ALCAMAC" was the particulate hydrotalcite represented by a chemical formula, $Mg_6Al_2(OH)_{16}(CO_3).4H_2O$.

Testing method.

Test groups.

| Control | 6 rats |
|---|---|
| Particulate composite hydrotalcite, 100 mg/Kg | 6 rats |
| Particulate hydrotalcite, 100 mg/Kg | 6 rats |

A rat fasted overnight was abdominally operated under anesthesia with pentobarbital sodium (40 mg/Kg, i.p.), and 30 µL of 20% acetic acid was injected into the submucous coat in the boundary between the body of stomach (area) and the vestibular regio of the pylorus from the side of the serous membrane to prepare ulcer due to acetic acid. Three days after the ulcer models were prepared, the rats were grouped, and the medicines to be tested were orally administered one time a day for 10 days in an amount of 100 mg/kg each time. The day after the day of final administration, the stomach was removed under the anesthesia with pentobarbital sodium (40 mg/Kg, i.p.) to measure the long diameter×short diameter (mm) of the ulcer, and the area ($mm^2$) thereof was regarded to be the damage factor, and was expressed as an average value±standard error of 6 rats. The results were as shown in Table 3.

The results prove that the particulate composite hydrotalcite of the present invention works effectively.

TABLE 3

| Run No. (Medicine) | Doses (mg/kg, p.o.) | Number of rats | Damaged area in the stomach after the administration of medicine (lesions area) ($mm^2$) | Inhibition factor (%) |
|---|---|---|---|---|
| Control[a] | — | 6 | 16.6 ± 1.3 | — |
| Ex. 12 (comp. hydrotalcite) | 100 | 6 | 10.3 ± 2.1 | 38 |
| Comp. Ex. 1 (ALCAMAC) | 100 | 6 | 17.0 ± 2.3 | −2 |

[a] 0.5% methyl cellulose (5 mL/kg)

EXAMPLE 18

Pharmacological test.

Effect upon the stomach ulcer was examined in the same manner as in Example 17 by using male rats (SPF) and the particulate composite hydrotalcite obtained in Example 15.

The results were as shown in Table 4.

EXAMPLE 19

Pharmacological test.

Effect upon the stomach ulcer was examined in the same manner as in Example 17 by using male rats (SPF) and the particulate composite hydrotalcite obtained in Example 9.

The results were as shown in Table 4.

The results prove that the particulate composite hydrotalcites of Example 9 and Example 15 works particularly effectively.

TABLE 4

| Run No. | Medicine | Doses (mg/kg, p.o.) | Number of rats | Damaged area in the stomach after the administration of medicine (lesions area) ($mm^2$) | Inhibition factor (%) |
|---|---|---|---|---|---|
| Control | [a] | — | 6 | 9.4 ± 1.1 | — |
| Ex. 18 | Ex. 15[b] | 100 | 6 | 5.1 ± 1.7 | 46 |
| Ex. 19 | Ex. 9[b] | 100 | 6 | 3.5 ± 0.7 | 63 |

[a] 0.5% methyl cellulose (5 mL/kg)
[b] (particulate composite hydrotalcite)

EXAMPLE 20

Pharmacological test.

Effect upon the stomach ulcer was examined in the same manner as in Example 17 by using male rats (SPF) and the particulate composite hydrotalcite obtained in Example 16.

The results were as shown in Table 5.

The results prove that the particulate composite hydrotalcite of the invention works effectively.

TABLE 5

| Run No. | Medicine | Doses (mg/kg, p.o.) | Number of rats | Damaged area in the stomach after the administration of medicine (lesions area) ($mm^2$) | Inhibition factor (%) |
|---|---|---|---|---|---|
| Control | [a] | — | 6 | 9.4 ± 1.1 | — |
| Ex. 20 | Ex. 16[b] | 100 | 6 | 5.6 ± 0.7 | 40 |

[a] 0.5% methyl cellulose (5 mL/kg)
[b] (particulate composite hydrotalcite)

COMPARATIVE EXAMPLE 3

Pharmacological test.

Effect upon the stomach ulcer was examined in the same manner as in Example 17 by using male rats (SPF) and the mixed sample (mixture of the particulate hydrotalcite and the particulate zinc oxide; zinc (Zn) content of 1% by weight) obtained in Comparative Example 2.

The results were as shown in Table 6.

The results prove that the mixed sample of Comparative Example 2 has no effect.

TABLE 6

| Run No. | Medicine | Doses (mg/kg, p.o.) | Number of rats | Damaged area in the stomach after the administration of medicine (lesions area) (mm$^2$) | Inhibition factor (%) |
|---|---|---|---|---|---|
| Control | a) | — | 6 | 10.1 ± 0.8 | — |
| Comp. Ex. 3 | Comp. Ex. 2 (ALCAMAC + ZnO) | 100 | 6 | 8.2 ± 1.2 | 19 | a): 0.5% methyl cellulose (5 mL/kg)

The invention claimed is:

1. A method of treating a peptic ulcer by orally administering an effective amount of a particulate composite hydrotalcite represented by the following formula (1) to a person suffering from the peptic ulcer $$(Mg_aZn_b)_{1-x}Al_x(OH)_2(A^{n-})_{x/n} \cdot mH_2O \quad (1)$$

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.1 \leq a < 1$, $0 < b \leq 0.5$, $0 \leq m < 1$.

2. The method of treating the peptic ulcer according to claim 1, wherein $A^{n-}$ in said formula (1) is $CO_3^{2-}$ or $SO_4^{2-}$.

3. The method of treating the peptic ulcer according to claim 1, wherein $A^{n-}$ in said formula (1) is $CO_3^{2-}$.

4. The method of treating the peptic ulcer according to claim 1, wherein x in said formula (1) satisfies $0.2 \leq x \leq 0.35$.

5. The method of treating the peptic ulcer according to claim 1, wherein b in said formula (1) satisfies $0.0005 \leq b \leq 0.2$.

6. The method of treating the peptic ulcer according to claim 1, wherein b in said formula (1) satisfies $0.005 \leq b \leq 0.1$.

7. The method of treating the peptic ulcer according to claim 1, wherein a in said formula (1) satisfies $0.2 \leq a \leq 0.9$.

* * * * *